United States Patent
Sa'ar et al.

(10) Patent No.: US 10,309,958 B2
(45) Date of Patent: Jun. 4, 2019

(54) METHOD AND APPARATUS FOR BACTERIAL MONITORING

(71) Applicants: YISSUM RESEARCH DEVELOPMENT COMPANY OF THE HEBREW UNIVERSITY OF JERUSALEM LTD., Jerusalem (IL); TECHNION RESEARCH & DEVELOPMENT FOUNDATION LIMITED, Haifa (IL)

(72) Inventors: Amir Sa'ar, Mevasseret Zion (IL); Ester Segal, Haifa (IL)

(73) Assignees: YISSUM RESEARCH DEVELOPMENT COMPANY OF THE HEBREW UNIVERSITY OF JERUSALEM LTD., Jerusalem (IL); TECHNION RESEARCH & DEVELOPMENT FOUNDATION LIMITED, Haifa (IL)

( * ) Notice: Subject to any disclaimer, the term of this patent is extended or adjusted under 35 U.S.C. 154(b) by 306 days.

(21) Appl. No.: 14/779,977

(22) PCT Filed: Mar. 25, 2014

(86) PCT No.: PCT/IL2014/050317
§ 371 (c)(1),
(2) Date: Sep. 25, 2015

(87) PCT Pub. No.: WO2014/155381
PCT Pub. Date: Oct. 2, 2014

(65) Prior Publication Data
US 2016/0061822 A1     Mar. 3, 2016

Related U.S. Application Data

(60) Provisional application No. 61/804,775, filed on Mar. 25, 2013.

(51) Int. Cl.
    *G01N 21/47*     (2006.01)
    *G01N 33/53*     (2006.01)
    (Continued)

(52) U.S. Cl.
    CPC ......... *G01N 33/5302* (2013.01); *G01D 5/266* (2013.01); *G01N 21/4738* (2013.01);
    (Continued)

(58) Field of Classification Search
    CPC ........ B01L 2300/0829; G01N 33/5302; G01N 21/4788
    See application file for complete search history.

(56) References Cited

U.S. PATENT DOCUMENTS 6,248,539 B1    6/2001    Ghadiri et al.
7,759,129 B2    7/2010    Sailor et al.
(Continued)

FOREIGN PATENT DOCUMENTS

WO     2010099805 A1    9/2010
WO     2013165398 A1    11/2013

OTHER PUBLICATIONS

Pacholski C et al, Biosensing using porous silicon double-layer interferometers: Reflective interferometric fourier transform spectroscopy, Journal of the American Chemical Society, Aug. 24, 2005, pp. 11636-11645, vol. 127, No. 33, American Chemical Society, US.
(Continued)

*Primary Examiner* — Jonathan M Hurst
(74) *Attorney, Agent, or Firm* — The Roy Gross Law Firm, LLC; Roy Gross (57) ABSTRACT

A system for detecting target elements such as bacteria in a host analyte, comprising a substrate with an ordered array of wells having diameters to fit the size of the targets. The substrate may be a periodic macro-PSi array structure (MP-SiAS) illuminated with a broadband source. The reflected
(Continued)

light spectrum diffracted from the substrate is optically analyzed to provide the effective optical depth of the wells. Fast Fourier Transform analysis may be used for the optical analysis. Entry of target elements into wells is detected by the change in the effective optical depths of the wells. Micro-organisms as large as bacteria and viruses having dimensions comparable with the wavelength of the illumination can thus be detected. Wells with an inner section impenetrable by the target cells enables compensation for environmental changes. The detection may be performed in real time, such that production line bacterial monitoring may be achieved.

22 Claims, 7 Drawing Sheets (51) Int. Cl.
 G01D 5/26 (2006.01)
 G01N 21/85 (2006.01)
(52) U.S. Cl.
 CPC ......... *G01N 21/4788* (2013.01); *G01N 21/85* (2013.01); *G01N 2201/0446* (2013.01); *G01N 2201/061* (2013.01)

(56) References Cited

U.S. PATENT DOCUMENTS

| 8,274,643 | B2 | 9/2012 | Sailor et al. |
| 2002/0192680 | A1 | 12/2002 | Chan et al. |
| 2003/0027328 | A1 | 2/2003 | Cunningham et al. |
| 2006/0234391 | A1 | 10/2006 | Weiss et al. |
| 2006/0255008 | A1 | 11/2006 | Link et al. |
| 2006/0276047 | A1* | 12/2006 | Ouyang ........... G01N 33/54373 438/753 |
| 2007/0108465 | A1* | 5/2007 | Pacholski ............ G01N 21/55 257/103 |
| 2009/0180932 | A1 | 7/2009 | Angeley et al. |
| 2010/0246007 | A1 | 9/2010 | Moon et al. |
| 2010/0279886 | A1 | 11/2010 | Fauchet et al. |
| 2012/0214707 | A1 | 8/2012 | Ymeti et al. |
| 2012/0268823 | A1 | 10/2012 | Morhard et al. |
| 2013/0338303 | A1 | 12/2013 | Quint et al. |
| 2014/0011223 | A1 | 1/2014 | Sjong et al. |

OTHER PUBLICATIONS

X.G. Zhang, Morphology and Formation Mechanisms of Porous Silicon, Journal of the Electrochemical Society, Dec. 9, 2003, p. C69, XPO55309486, vol. 151, No. 1.

M. Holgado et al, Micro-nano photonic biosensors scalable at the wafer level, Optical Sensing II, Feb. 12, 2009, p. 72200P, XPO55311429, vol. 7220, US.

Jane A et al, Porous silicon biosensors on the advance, Trends in Biotechnology, Feb. 27, 2009, pp. 230-239, XP026029660, vol. 27, No. 4, Elsevier Publications, Cambridge, GB.

PCT International Search Report and Written Opinion for PCT/IL2014050317, dated Jul. 11, 2014.

Supplementary European Search Report for EP 14773472, dated Oct. 26, 2016.

* cited by examiner

| SAMPLE # | PERIODICITY OF PORES [μm] | PORES DEPTH [μm] | ΔEOT (nm) | ΔEOT/ EOT | FILL FRACTION BY MODEL [%] | FILL FRACTION BY CLSM [%] |
|---|---|---|---|---|---|---|
| 1 | 4 | 3.5 | 45±5 | 0.0048 | 25±7 | 21±1 |
| 2 | 4 | 4 | 38±10 | 0.0036 | 8±4 | 7±3 |
| 3 | 2.5 | 2.5 | 8±2 | 0.0013 | 2±1 | 1.6±0.4 |
| 4 | 2.5 | 7.5 | 4±2 | 0.0002 | 4±2 | 3±1 |

METHOD AND APPARATUS FOR BACTERIAL MONITORING

CROSS-REFERENCE TO RELATED APPLICATIONS

This application is a U.S. National Phase Application under 35 U.S.C. 371 of International Application No. PCT/IL2014/050317, which has an international filing date of Mar. 25, 2014, and which claims the benefit of priority from U.S. Provisional Patent Application No. 61/804,775, filed Mar. 25, 2013, the disclosures of which are incorporated herein by reference in their entirety.

FIELD OF THE INVENTION

The present invention relates to the field of the detection and measurement of bacterial contamination in samples, especially by the use of optical monitoring.

BACKGROUND OF THE INVENTION

Biosensing is an important field in industry, and especially in the food industry, where the detection and monitoring of the levels of bio-contaminants, such as bacterial levels in food products, is of critical importance in maintaining modern health standards. In the food industry, the need for constant monitoring of products coming off production lines is particularly important and problematic, since any production fault resulting in bio-contamination of the products must be detected before products are shipped for marketing. This is currently often done by means of testing cultures grown from samples from each production line and batch. However, because of the time taken to grow and tests such cultures, even using modern accelerated culture growth and measurement techniques, a large number of products may have been produced and packed ready for shipping before the contamination is detected, thus leading to considerable loss. There exist technologies, such as surface plasma resonance (SPR) for instance, which enable constant monitoring of the bio-contaminant levels in products, but such technologies are costly—a typical installation costing many tens of thousands of dollars. Because of the large number of different products produced on different production lines, such bio-sensing technologies are often prohibitively expensive for general use in the food industry, and there appear to exist no low cost bio-sensing equipment which can perform cost effective widespread online monitoring of food products.

In recent years, porous Si (hereinafter PSi) has emerged as a promising nanomaterial for bio-sensing applications, and for sensing other targets with nanoscale dimensions. Common PSi-based optical sensors and biosensors consist of thin films of either nano-pores (typically of dimensions less than 20 nm) or meso-pores (typically in the range of 20-100 nm) which thus have cross sectional dimensions much smaller than the optical wavelengths used. The pores are generally randomly generated during production of the thin film device. The operation of these sensors is based on replacing the media in the pores and/or infiltrating with the target analyte, and observing the resulting changes of optical reflectivity. A change in the effective refractive index of the PSi film is manifested as a wavelength shift in the reflectivity spectrum. Only target molecules which penetrate into these nanostructures, can be detected. Indeed, sensing and biosensing of various chemical and biological analytes, such as fluorescent molecules, organophosphates, volatile organic compounds, DNA, and proteins have been successfully demonstrated. Many of these studies employ the method of reflective interferometric Fourier transform spectroscopy (RIFTS) to monitor biological interaction within mesoporous Si thin films.

Such filled or partially filled, randomly located pores can be viewed as simply having a different effective refractive index from that of unfilled pores, because the pores are much smaller than the optical wavelength. Consequently, the random nature of the pores does not result in scatter of the light, but rather in an averaging out of the overall reflected light from the combination of the silicon substrate and the pores, both filled and unfilled. However, this detection scheme is not applicable for targeting large biological or other species, such as those ranging in size of from approximately a few hundreds of nanometers up to several microns and more, including cells, bacteria and viruses. If porous silicon is produced having such larger pores, the substrate becomes a material known as "black silicon", which appears as such because it strongly scatters light from the random distribution of the large sized pores. Essentially all of the incident light is randomly scattered by the pores and is absorbed in the medium, such that it cannot be used for sensing. Therefore, the prior art porous silicon technology cannot be used for sensing or bio-sensing of larger targets of sizes which are a significant fraction of the wavelength of the light used for the sensing.

There exist alternative methods which monitor changes in the intensity of the reflectivity spectrum upon direct capture of larger cellular targets on top of the biosensor surface, rather than in the pores thereof. However, these types of sensors are limited, since intensity changes of the reflectivity spectrum may arise from unpredictable sources, such as environmental effects and non-specific binding events. In addition, the sensitivity may be low because such surface-binding sensors do not take advantage of the large porous volume.

In recent years attempts have been made to develop new bioassays and biosensors for the rapid detection of bacteria in general, and pathogenic bacteria in particular. However, despite the significant progress in the field, current technologies lack the ability to detect microorganisms in "real time" or outside the laboratory environment There therefore exists a serious need for a detection method and apparatus which overcomes at least some of the disadvantages of prior art systems and methods, and in particular, is able to perform continuous monitoring of the level of large biological contamination species, such as living cells, pathogenic bacteria, spores and viruses, or of other species of similar size, namely dimensions generally equal to or greater than the wavelength of visible light.

The disclosures of each of the publications mentioned in this section and in other sections of the specification, are hereby incorporated by reference, each in its entirety.

SUMMARY

The present disclosure describes new exemplary methods and systems for the detection and measurement of the concentration of large targets such as micro-organism in the form of cells, bacteria or viruses, or of other large particular biological or other targets.

The methods and systems of the present disclosure are based on the capture of the target elements in pores or micro-compartments, and can be summarized briefly by noting the following characteristics thereof:

(a) Such targets are trapped in pores or micro compartments having sizes selected to accommodate the intended targets, and hence should be at least as large as the targets. In addition, the surface of the micro-compartments or pores can be modified or tailored to enhance the capture and adhesion of the cells to the pores. For example, the surface chemistry of the pores, the roughness of the pore surface and its wettability (either hydrophobic or hydrophilic), can be adjusted for the specific type of target cells and bacteria to be detected.

(b) The order of the pores/compartments is arranged so that light incident thereupon is scattered or reflected, but not randomly, but rather into a set of diffraction orders, such as a diffraction pattern typical of an optical grating. In this case, the zero order of the diffraction pattern as measured by the backscattered light, allows direct sensing of the effective optical thickness (EOT) of the pores/micro compartments. Hence, the zero order of the diffracted light is expected to show an interference pattern that is determined by the EOT of the pores. The depth of the pores can be adjusted to allow sensitive detection of the EOT.

(c) Sensing is achieved by using the changes in the refractive index of the medium in the pores to indicate the presence of target cells within the pores. The medium is usually a liquid or a buffer used to maintain the target cells, and change in the refractive index thereof changes the EOT of the light entering and being reflected from the pores.

(d) One particular method, but not necessarily the only one, to detect the EOT, particularly useful when the EOT is larger than the optical wavelength of the light, EOT>$\lambda$, is by use of Fast Fourier Transform analysis, whereby the spectrum of the reflected light is Fourier transformed to obtain a single intensity peak, whose position characterizes the EOT.

(e) A particularly convenient arrangement for implementing the above described apparatus and methods uses a 2-dimensional periodic Macro-Porous Silicon Array Structure (MPSiAS). A variety of fabrication techniques can be utilized for the fabrication of such an MPSiAS matrix, such as an electrochemical method or a dry etching method using Reactive-Ion Etching (RIE). It is to be understood, however, that the methods and structures can be implemented by other materials and platforms, such as other semiconductors, organic polymers, gels, glasses and even metallic surfaces.

Consideration is now made of more details of the above described features. Since the size of the targets is equal to or larger than the wavelengths of commonly used light sources (including ultra-violet, visible and near-infrared spectral ranges), prior art PSi substrates with pore sizes large enough to accommodate these targets cannot be used, since, as previously mentioned, the incident optical illumination on a substrate containing a non-ordered assembly of such large pores would result in random scattered light, because of the large size distribution and the random position of the pores. In the apparatus and methods of the present disclosure, a two-dimensional (2D) ordered array of pores or microstructures is used, illuminated in a direction perpendicular to the plane of the pores. This structure overcomes the prior art problems of optical measurement on pores having sizes larger than the wavelength of the light used for the measurements. Such a structure is effectively a lamellar phase grating, and can be conveniently implemented in the form of a 2D periodic macro-PSi array structure (MPSiAS), with pore diameters configured to fit the size of the target. For example, if the typical size of bacterial cells to be captured is in the range of 0.5 to 2$\mu$, the size of the pores or micro-compartments can be fabricated to be in the range of 1 to 10$\mu$, to accommodate those cells. These structures are then used as the optical sensing platform for the detection of the target, such as bacteria cells. Such periodic structures of PSi photonic crystals, with pore diameters comparable in size to that of bacteria cells may be fabricated by photolithography followed by either electrochemical anodization process (using hydro-fluoric based solution) or by dry etching techniques such as reactive-ion-etching (RIE), to etch the pattern of the pores into standard, commercially available silicon wafers. Both methods are well known in the semiconductor industry and are compatible with standard silicon processing techniques. The resulting PSi structures act as a lamellar or a phase grating that scatters reflected light into a set of diffraction orders at various angles according to the strict relationship between the periodicity of the grating and the optical wavelength as determined by physical optics. If the reflected light is collected normal to the pores' surface, only the zero-order diffraction is measured. This is usually achieved by using optical lenses having the appropriate f-number and optical fibers for delivering the incident light and collecting the backscattered, zero-order reflected light. In this case, only a phase delay associated with the depth of the pores contributes to the interference pattern created by the backscattered light. This interference pattern is exploited for the measurements of the effective optical thickness (EOT) of the pores.

The presence of target cells within the pores changes the refractive index of the medium in the pores, thus changing the effective optical thickness (EOT) of the pores in the laminar grating. The greater the percentage of macro-pores filled with target cells, the greater the change in the EOT. Thus, measurement of the EOT enables the concentration of target cells in the host solution to be found. Measurement of the EOT of the lamellar grating can be performed in real-time, by illuminating the MPSiAS layer with a broadband light source. The reflected light spectrum over the wavelength range to be measured is a complex combination of the reflections from the top surface of the MPSiAS and from the light reflected after passing through the pores and being reflected from their bottom surface. One convenient method by which the reflected spectrum can be measured is by performing Fast Fourier transform (FFT) analysis on this spectrum, by which a single intensity peak is obtained, whose position characterizes the effective EOT of the layer. However, it is to be understood that any other spectral analysis method, or direct optical path difference method may be used. This provides a measurement of the percentage of pores filled by the target cells (sometime called, "the filling factor" of the pores). Therefore, when the host analyte in the pores are replaced by the target cells to be detected, the EOT changes since the refractive index of the optical media within the wells changes, and hence the position of the output peak of the FFT analysis also changes. The greater the shift in the position of the peak, the higher the concentration of the target cells in the pores. Since the optical measurements can be performed essentially instantaneously, these devices thus provide an effectively real-time measurement of the concentration of target cells in the host solution, the only delay being the time to effectively fill the ordered pore structure with the target cells of the host solution. Furthermore, since the PSi array structure can be readily manufactured by conventional semiconductor technology, the array chip can be provided at low cost for large production runs. Additionally, the optical measurement system is also readily available in the form of a miniature spectrometer, such that the cost of the monitoring system could be substantially less, perhaps by two orders of magnitude, than prior art systems currently used for detecting bio-contamination.

In order to combat the effect of environmental changes, which would result in the shift of the EOT even without any change in the content of the pore structures, a double pore structure can be used, in which the cross sectional dimensions of the inner end of the well, that being the end further from the surface exposed to the host solution, are smaller than the cross sectional dimensions of the outer section of the well. In such a situation, the target cells may be trapped in the outer section, but cannot penetrate the inner narrower section of the wells. However, the host solution does penetrate the inner section and is measured independently of the presence or absence of trapped target cells in the host solution. For such a double well structure, three FFT peaks are detected associated with the effective optical path differences (i) from the surface of the substrate to the bottom of the inner section, (ii) from the surface to the bottom of the outer section, and (iii) between the bottoms of the inner and outer sections. Since the target cell concentration is determined by change in the EOTs (i) and (ii) relative to EOT (iii), while environmental change shifts, to first order, all three of the EOTs equally, the peak associated with the inner section of the wells, EOT (iii) can be used as a base line marker to compensate for environmental change, in particular, change in the ambient temperature. Furthermore, by use of suitable selective coatings, the inner sections can be used to detect secretions from target cells trapped in the outer sections of the wells.

The devices and methods described hereinabove enable the determination of the presence of the target elements trapped in the wells of the MPSiAS, and a quantitative estimate of their comparative level in the host analyte. However, although this may be sufficient information for use in some applications where the target identity is unique, in many applications there could be a number of different target elements, all having similar dimensions, or smaller dimension than the target element, which would enable them to be trapped within the wells, such that the optical analysis performed would not provide information about the specific target identification. Thus, for instance, in a system intended to determine the presence of bacterial pathogens, such as certain strains of *E. coli*, the presence of other bacteria in the analyte, which too could be trapped in the pores of the device, would render the measurement problematic with regard to determining the level of *E. coli*. Thus, in order to perform such specific assays, it may be necessary to provide some form of recognition mechanism in order to specifically capture the target micro-organisms which are intended to be detected and measured, thus providing a level of selectivity to the device. Thus, for instance, the surface chemistry of the walls of the wells may be treated to provide a capture probe to trap the micro-organisms which are intended to be measured by the device. They will then remain trapped, while other bacteria and cells will not. The required effect could be obtained by coating with specific antibodies or aptamers or other peptides having a high affinity to the target microorganism. A bio-mechanism may then be required for ensuring the orientation of the capture probes in the wells such that they trap the incoming bacteria or other cells or organisms. The recognition moiety used will generally be specific for the microorganism to be detected and measured. Therefore, a range of different detection devices can be provided, each being treated with a recognition moiety adapted to the microorganism which it is intended to measure. In principle, the biosensor described in the present disclosure may contain several or even an array of 2D-MPSiAS (each one could be few hundred of μm by few hundred of μm, up to few mm by few mm). Each one of these MPSiAS can be functionalized for selective detection of a different type of micro-organism, so that a multi-level of bacteria's recognition can be accomplished by this sensor.

The MPSiAS devices of the present disclosure can also be used for executing a method of determining the viability of micro-organisms, i.e. in order to differentiate between live and dead cells. Thus, if the device is used for capturing a certain type of bacterial cell, introduction of a growth medium will result in multiplication of the number of live bacteria. This will be reflected in a shift in the EOT signal position, as the effective refractive index of the pores increases.

Although the arrays in this disclosure have been described as being formed in silicon, this being a common and convenient material from which the arrays can be formed, it is to be understand that use of silicon substrates is not intended to limit the invention in any way, and that the invention can be implemented using other materials such as glass, plastic substrates, and fabrication techniques to those described in this disclosure. However, one possible advantage of silicon is the ability to integrate other electronic devices and circuits with the MPSiAS sensor on the same chip; for example, wireless communication capabilities for remote sensing applications.

Furthermore, although the methods and structures of this disclosure are generally described as applied to the detection of biological targets having dimensions of the same order as or somewhat larger than the wavelength of the light used for the detection, it is to be understood that these methods and structures are not intended to be limited to such biological targets, but are understood to be applicable to the detection of targets of suitable size of any type, whether biological or not. Such other applications could be found in the fields of water technologies, environmental pollution measurement, chemical industries, and others.

Furthermore, since white light or broadband sources having a range of wavelengths should be used in the apparatus described in the present disclosure, and for performing the methods of the present application, and such sources may have wavelengths which stretch out well beyond the region in which the spectral detection is performed, it is to be understood that reference, both in the disclosure and as claimed, to the wavelength of light or illumination being used to perform the detection is understood to refer to wavelengths where the majority of the energy of the source is concentrated, such as the wavelength at the point of peak intensity, or the mean wavelength of the spectral region containing the majority of the optical intensity, or the wavelength of maximum sensitivity of the detector, or similar definitions. In any event, the term wavelength of the incident illumination and expressions having similar meaning is not intended to include limitations based on wavelengths at extreme ends of the source's emitted spectrum, where the detection efficiency or the illumination level is impractically low.

Additionally, the traps into which the target elements enter and are captured, and whose effective optical depths are measured, have been variously described in this disclosure as pores, micro-compartments and wells, all of which are understood to relate to the same feature. The term well is used in the claims as a simple generic term to represent any of these features.

There is thus provided in accordance with an exemplary implementation of the devices described in this disclosure, a system for detecting target elements in a host analyte, the system comprising:
(i) a substrate containing an ordered array of wells formed in its surface, at least some of the wells having lateral dimensions such that the target elements can fit therein,
(ii) a broadband illumination source emitting a range of wavelengths, disposed so as to illuminate the surface of the substrate,
(iii) an optical detector disposed such that it collects light diffracted from the substrate, and outputs a reflected spectrum signal, and
(iv) a signal processing unit, adapted to analyze the reflected spectrum signal to provide a measure of the effective optical depth of the wells,
wherein at least some of the wells have a lateral dimension at least as large as the wavelengths of the illumination source detected by the optical detector.

In such a system, the signal processing unit may analyze the reflected spectrum signal using the Fast Fourier Transform. In such a case, the effective optical depth is determined from the position of a peak obtained from the results of that Fast Fourier transform analysis on the reflected spectrum. Furthermore, the optical detector may be disposed normal to the substrate, such that it collects diffracted light of zero order from the substrate.

Additionally, in alternative implementations of the above-described systems, the effective optical depth of the wells may provide an indication of the concentration of the target elements captured within the array of wells, and hence also an indication of the concentration of the target elements in the analyte.

In any of the above described systems, the ordered array of wells may comprise a lamellar photonic crystal grating. Additionally, the substrate may a silicon chip, and the ordered array of wells may be constructed by microelectronic fabrication processes.

Additional implementations may involve a system such as those previously described, in which the target elements are bacterial cells having dimensions larger than the wavelengths of the illumination source detected by the optical detector element. The wells may comprise capture probes having a high affinity to the target cells intended to be measured by the system. Such capture probes may be coated on the walls of the wells. As specific examples, the target elements may be micro-organisms, and the capture probes may then be any one of antibodies, aptamers or other peptides. These microorganisms may be bacterial cells, and the capture probes specific antibodies. Furthermore, the wells may incorporate a cell nutrient supply, such that the growth of the microorganisms can be observed after application of the nutrient supply. Lack of growth of the microorganism after application of the nutrient supply can then be used as an indication that the microorganism is generally dead. Furthermore, in any of these systems, at least some of the wells may include a recognition moiety adapted to the target elements to be detected. If so, then the substrate may comprise at least two different regions, the wells in each of the regions including a different recognition moiety, such that each of the different regions can detect different target elements concurrently.

In general, any of the above described systems may be adapted to provide real time detection of microorganisms.

Another example implementation can involve a system such as any of those previously described, in which at least some of the wells have at least two sequential sections having different lateral dimensions, and wherein a second section, further from the surface than a first section, has a lateral dimension less than that of the first section. In such a configuration, the dimensions of the second section may be such that the target elements cannot penetrate the second section, while the host analyte can. In this case, change of the measured effective optical depth of the second section of at least some wells may be utilized as a marker to compensate for changes in environmental conditions that cause the effective optical depth of both of the first and second sections to change. The second section may be provided with sensitivity to a material which targets trapped in the first section may secrete. In this case, the sensitivity may be utilized to provide further information regarding the level of targets trapped in the first sections of the wells.

Yet other implementations perform a method for detecting target elements in a host analyte, the method comprising:
(i) providing a substrate containing an ordered array of wells formed in its surface,
(ii) illuminating the surface of the substrate with broadband illumination,
(iii) detecting light diffracted from the substrate and generating therefrom a reflected spectrum signal, and
(iv) determining from the reflected spectrum signal a measure of the effective optical depth of the wells,
wherein at least some of the wells have a lateral dimension larger than the wavelength of the detected broadband illumination.

In such a method, the step of determining from the reflected spectrum signal a measure of the effective optical depth of the wells, may be performed by Fast Fourier Transformation analysis. In any case, the detecting may be performed normal to the substrate, such that light of zero order diffracted from the substrate is detected. The target elements may be bacteria, and the host analyte may be any one of water, a buffer solution, blood, urine or a solution derived during a food process.

In some implementations of this method, at least some of the wells may have at least two sequential sections having different lateral dimensions, and a second section, further from the surface than a first section, should have a lateral dimension less than that of the first section. In such a method, the dimensions of the second section may be such that the target elements cannot penetrate the second section, while the host analyte can. Any such method may further comprise the step of detecting change in the effective optical depth of the second section of at least some of the wells, such that compensation can be made for changes in environmental conditions that cause the effective optical depth of both of the first and second sections to change.

BRIEF DESCRIPTION OF THE DRAWINGS

The present invention will be understood and appreciated more fully from the following detailed description, taken in conjunction with the drawings in which.

DETAILED DESCRIPTION

Figure 1A:
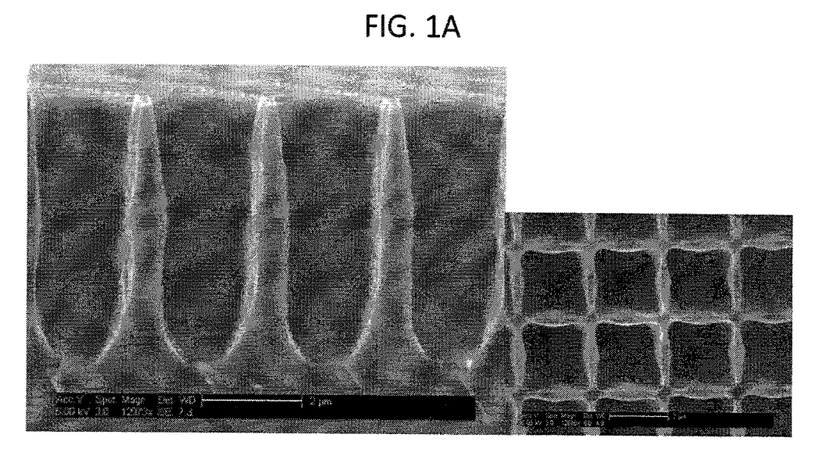
FIGS. 1A and 1B show SEM micrograph views of a two-dimensional periodic macro-PSi array structure (MP-SiAS) of the type described in this disclosure.
Figure 1B:
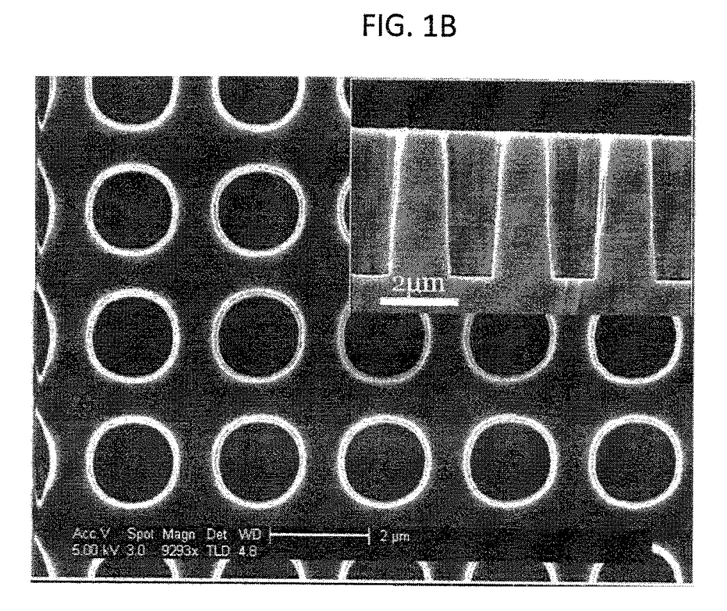

Reference is now made to FIG. 1A, which illustrates a cross-sectional SEM micrograph view and, in the insert, a top view, of an exemplary two-dimensional (2D) periodic macro-PSi array structure (MPSiAS), having a pore diameter adapted to fit the size of the target bacteria cells. The structure shown in FIG. 1A is of an array fabricated by electrochemical etching after photolithography. For the purpose of describing the systems and methods of the present disclosure, the non-limiting example used in this detailed description is of a substrate structure having pores suitable in size for the detection of *E. coli* K-12 bacteria—which have diameters of 0.8 to 2 μm. The periodicity of the structure shown in FIG. 1A is about 3 μm. FIG. 1B shows a plan and cross-sectional SEM micrograph view an example of an MPSiAS produced using dry-etching as an alternative fabrication technology. In this example, the periodicity of the structure is about 3 μm.

Figure 1C:
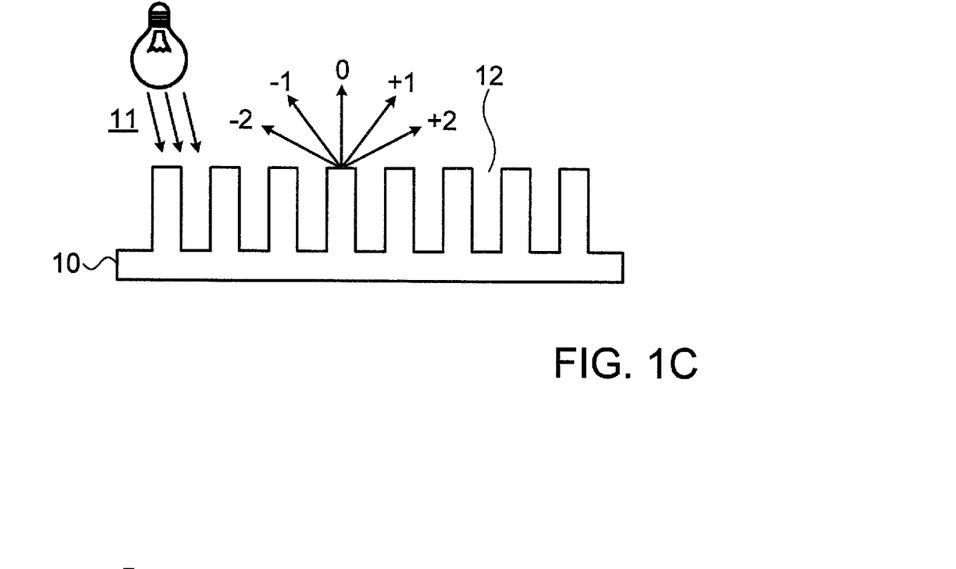
FIG. 1C illustrates schematically an exemplary system for using such a structure for detecting micro-organisms, as disclosed in the present application.

Reference is now made to FIG. 1C which illustrates schematically how the ordered array of wells 12 in the MPSiAS substrate 10 acts as a lamellar (or a phase) grating that reflects the incident light 11 falling on the structure into a set of diffraction orders at various angles according to the relationship between the periodicity of the grating and the optical wavelength. For light collected normal to the array surface, only the zero-order diffraction is measured, i.e. backscattered light having θ=0, where θ is the diffraction angle, yielding the following expression for the intensity I of the zero-order reflected light:

$$I(\theta = 0) = I_0 \cos^2(\psi_0/2) \quad (1)$$

where $$2\psi_0 = 2\,kL = \frac{2\pi}{\lambda}(2n_0L) \quad (2)$$

and $\psi_0$ is the phase delay between the incident and the reflected beams, $\lambda$ is the free space optical wavelength, k is the wave number, L is the depth of the pores, $n_0$ is the refractive index of the medium filling the pores, and the term $2n_0L$ is thus the optical path difference between the top surface of the device and the bottom surface of the wells, referred to as the effective optical thickness (EOT) of the lamellar grating. By using phase gratings having fairly deep wells, typically of the order of several times to several tens of times the optical wavelength, an interference pattern between the light reflected from the top of the grating structure and from the bottom of the wells can be obtained, analogous to the spectral response obtained from Fabry Perot interference.

Figure 1D:
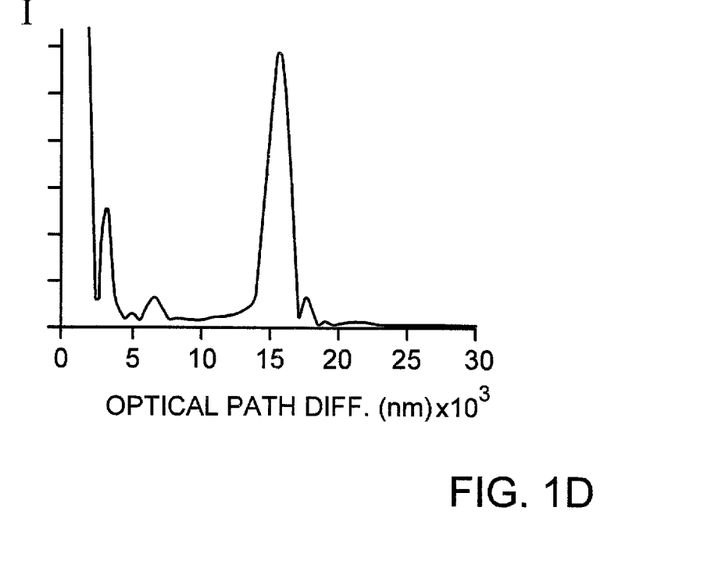
FIG. 1D is an exemplary graph showing the optical output used to determine the target concentration in the system of FIG. 1C.

In order to monitor the EOT of the device as the analyte solution is loaded, Fast Fourier transform (FFT) of the reflectivity spectrum from the MPSiAS layer is performed, resulting in a characteristic single peak, whose position is indicative of the EOT, as shown in the example graph of FIG. 1D of the reflected intensity I in arbitrary units, as a function of the optical path difference in nm. In the example shown in FIG. 1D, the optical path difference is seen to be of the order of 15 μm. Sensing is accomplished once bacteria penetrate into the macro-pores, inducing measurable changes in the EOT that can be monitored and quantified in real-time via RIFTS analysis. The magnitude of the peak is a function of the bacterial concentration above the macro-pore array.

Figure 1E:
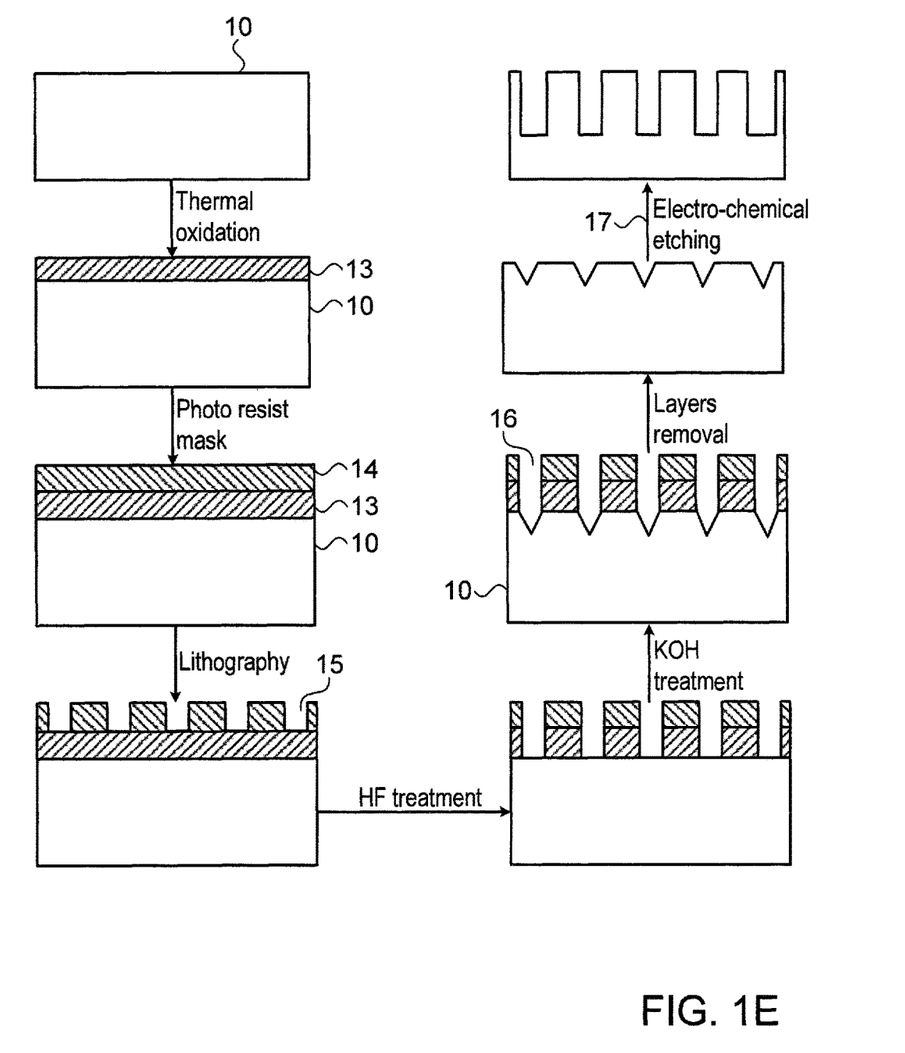
FIG. 1E illustrates schematically the steps for fabrication of a device of the type shown in FIG. 1A, using the electro-chemical etching method.

Reference is now made to FIG. 1E, which shows the fabrication chain for one exemplary process for fabricating the MPSiAS samples using photolithography followed by electrochemical anodization. As per conventional semiconductor processing, a $SiO_2$ layer 13 is formed on the top surface of the porous Si wafer 10 by thermal oxidation, followed by the photoresist layer 14 and a mask, typically formed by e-beam or holographic lithography, for defining the desired 2-D pore or well structure pattern. Next, the unexposed photoresist is removed to expose the etching pattern 15, followed by alkaline etching through the photolithographic oxide mask to generate a 2-dimensional pattern of inverted pyramid grooves 16 on top of the Si wafer. These inverted pyramids are used as the initial openings for forming the pore or well structures to the desired profile and depth. An electrochemical-etching process 17 can be advantageously used for this, performed under dark conditions, using a solution of hydrofluoric acid (HF) and dimethylformamide (DMF), at a constant current density, typically of the order of 30 mA/cm² for this type of substrate and well size. For the current example of *E. coli* detection, structures with a periodicity of 2.5 μm to 4 μm, and depths in the range of 2.5-7.5 μm can be used, to allow a facile entrapment of the bacteria cells within the array. Following anodization, which may typically be carried out under dark conditions, using an electrolyte solution of HF (49%) and DMF (1:7 v/v), at a constant current density of 30 mA/cm² for 125 s, the resulting freshly treated PSi is chemically oxidized, optionally in a 5:1:1 solution of $H_2O:NH_3:H_2O_2$ to create a hydrophilic porous $SiO_2$ matrix. Next, the oxidized MPSiAS samples may be modified in order to functionalize the porous surface specific or non-specific chemistries to target the microorganisms of interest; for example, by surface functionalization with positively charged groups; e.g., by using 2-aminopropyltriethoxy silane (2% APTES diluted in toluene). As most bacteria carry a net negative surface charge, adhesion of *E. coli* is promoted on the positively charged surfaces.

Figure 2:
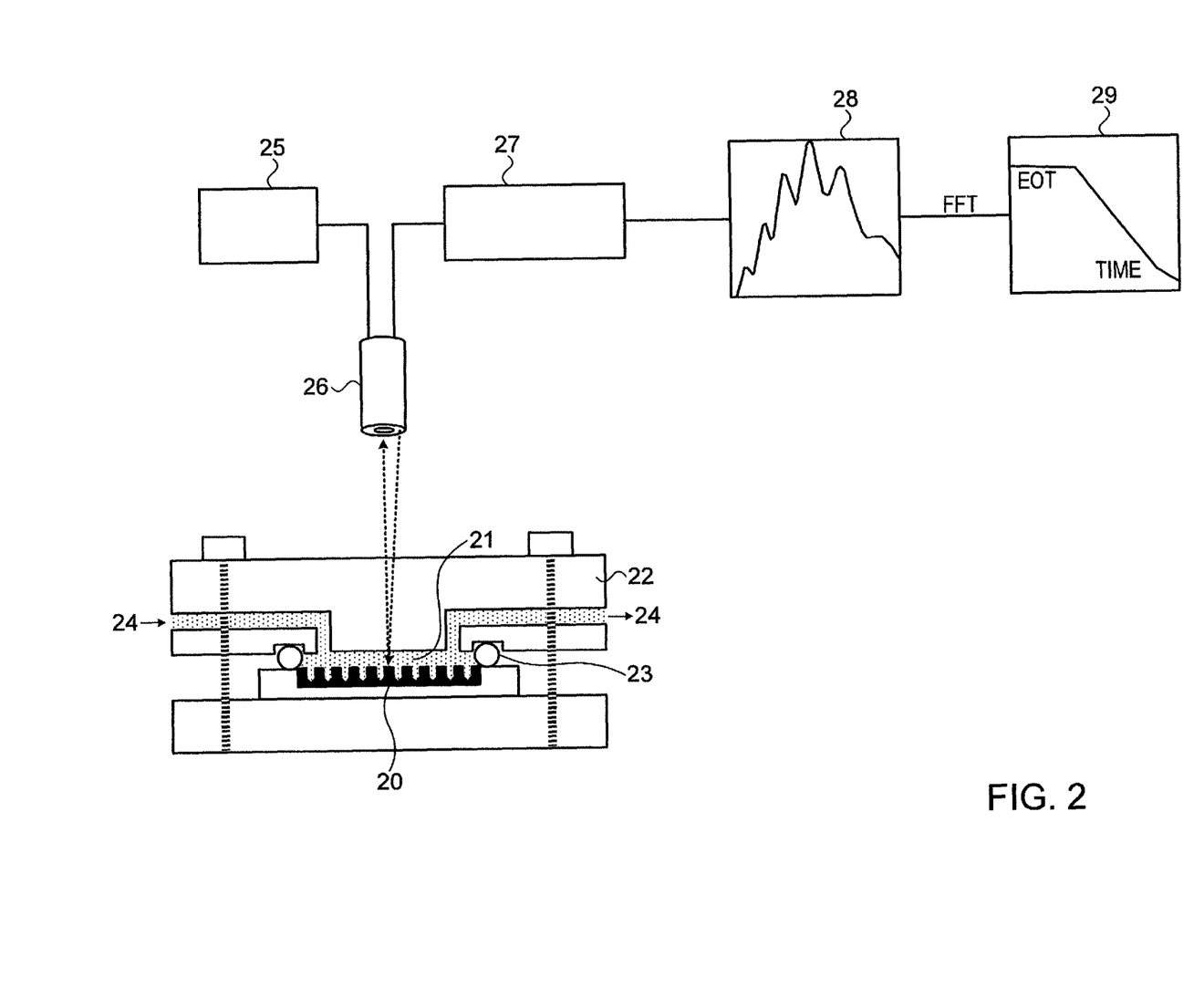
FIG. 2 illustrates schematically a bacterial monitoring system constructed using an MPSiAS of the type shown in FIG. 1A or 1B.

Reference is now made to FIG. 2, which illustrates schematically an exemplary bacterial monitoring system constructed to implement the methods described hereinabove. The MPSiAS 20 is shown mounted in the sampling chamber 21 of the sensor unit, which has a transparent cover 22 such as plexiglass sealed to the housing by means of an O-ring 23 to maintain the analyte host liquid within the sampling chamber. The sample liquid to be tested is flowed through the sampling chamber, as indicated by the arrows 24 in FIG. 2. The broadband light source, shown as a tungsten lamp 25 in FIG. 2, may be projected into the sampling chamber by means of a fiber optical feed, preferably a bifurcated fiber optical probe 26, and the light reflected from the silicon chip may be collected by the same fiber optical probe. The spectrum of this reflected light is now analyzed, which, in the exemplary system shown in FIG. 2, is performed by input into a mini spectrometer 27, such as the Ocean Optics USB 4000, available from Ocean Optics Inc. of Dunedin, Fla., USA, and the interferometric reflectance spectrum 28 is then FFT analyzed, conveniently by means of commercially available software, such as the Igor Pro, v. 6.03, available from Wavemetrics Inc, of Portland Oreg., USA. In the monitoring system shown in FIG. 2, the output 29 is shown as a continuous plot of the EOT displayed as a function of time, the change in the level of the EOT indicating a change in the level of target bacterial cells detected by the system. However, the processing system can be configured so that it provides a direct reading of the bacterial concentration. This requires prior calibration runs in which the bacterial concentration measured by the system is checked against another direct observation method, such as using confocal laser scanning microscopy.

Figure 3:
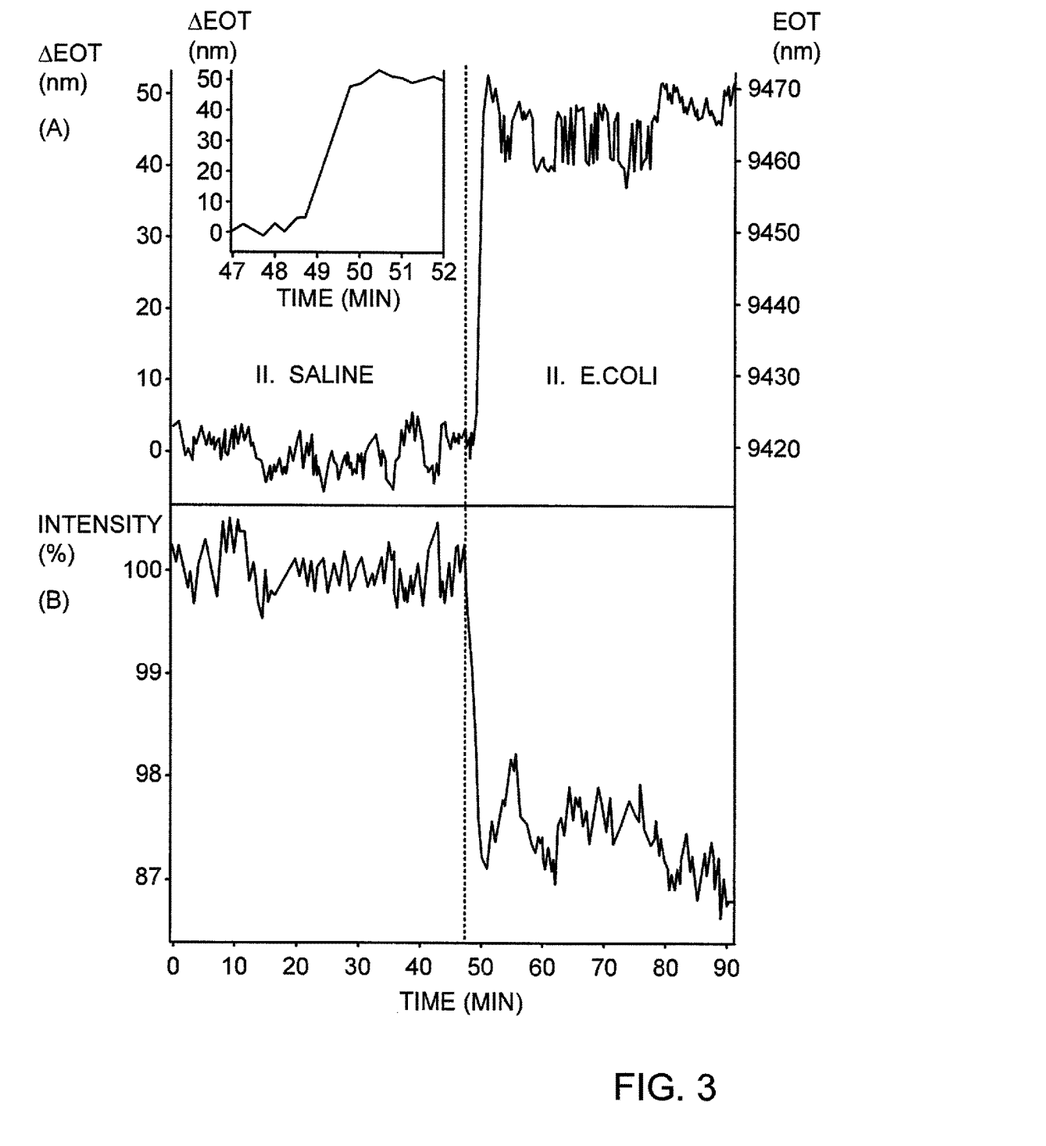
FIG. 3 shows an example of the output of a typical real time detection of the level of *E. coli* K12, using a system such as that described in FIG. 2.

Reference is now made to FIG. 3, which shows an example of the output of a typical real time detection of the level of *E. coli* K12, using a system such as that described in FIG. 2. The top graph of FIG. 3 shows the value of EOT measured as a function of elapsed time, while the bottom graph shows the reflectance intensity plotted as a function of time. The output data was recorded every 15 sec. In these plots, the changes in the FFT spectrum before and after the introduction of *E. coli* bacteria are depicted as a function of time. Sensing is accomplished by measuring the variation in the EOT and the intensity of the sensor once the bacteria cells are trapped inside the pores. In the upper plot, there is shown on the right hand ordinate, the measured EOT of the pores plotted as a function of time. The left hand ordinate shows the change, $\Delta$EOT measured. The graphs show an initial baseline plot with a constant flow of 0.85% w/v NaCl saline solution at 0.1 ml/min. At the point in time represented by minute 47, a bacterial suspension of $10^6$ cell/mL *E. coli* K12 in saline, was delivered to the detector system. A rapid increase in EOT of approximately 45 nm was observed. This EOT change is attributed to the entrapment of bacteria within the pores, leading to a refractive index increase. Simultaneously, in the lower graph of FIG. 3, the reflectance intensity is plotted as a function of time, and as is observed, a decrease in the reflectance intensity of about 3% occurs, probably due to light scattering induced by the bacteria cells. Optical studies demonstrate a detection limit of the order of $10^5$ cell mL$^{-1}$ for *E. coli*.

The inset graph of FIG. 3 shows a time-zoomed view of the EOT shift itself, to show the speed with which the bacterial level can be detected. As is observed, for this particular MPSiAS, the complete 45 nm. shift in EOT generated by the bacterial filling of the pores takes place in less than 1 minute, implying that an indication of the presence of a bacterial contaminant can be provided in a fraction of this time, thus illustrating the usefulness of the device for on-line, real time monitoring. Thus, the zero-order diffraction of the reflected light presents a spectral interference pattern according to the phase accumulated inside the pores, allowing for real-time detection of bacteria capture.

Figure 4A:
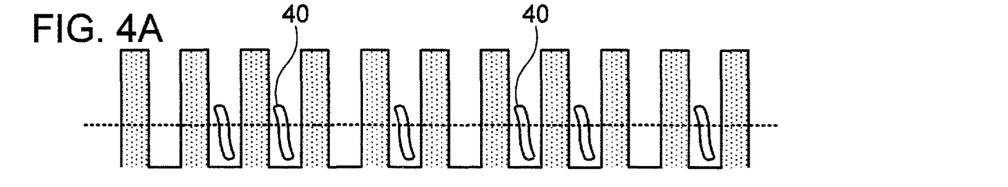
FIGS. 4A to 4C illustrate schematically a model by which the filling of the MPSiAS pores by the bacterial species is reflected by the change in effective optical depth measurements performed by the system.
Figure 4B:
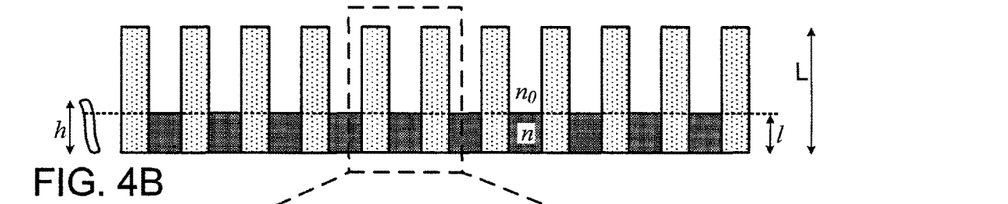
Figure 4C:
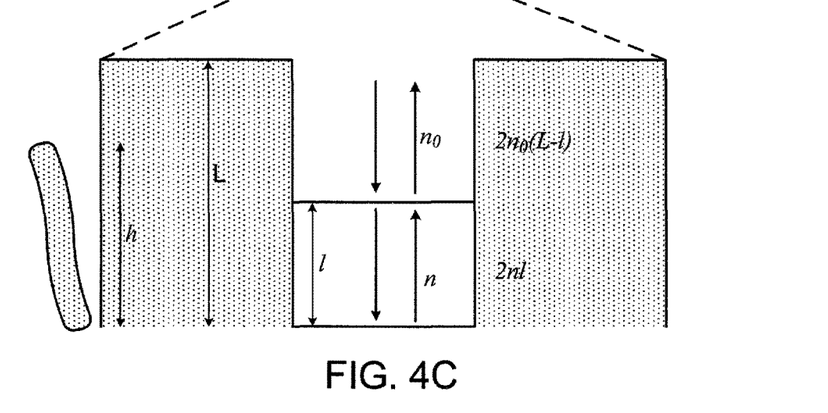

Reference is now made to the three parts of FIG. 4 which illustrate schematically a model showing the manner in which the filling of the MPSiAS pores by the bacterial or other large cell species is reflected by the change in effective optical depth measurements performed by the system.

The model attempts to correlate between the optical readout of the sensor i.e., EOT shift, and the bacteria concentration as expressed by the fill factor of the pores determined by direct microscopic investigation, such as by the Confocal Laser-Scanning Microscopy (CLSM) technique. From image analysis of the CLSM data, the relative number of pores occupied by bacteria can be quantified, this value being referred to as the 'fill fraction' of the MPSiAS. In the line (A) of FIG. 4, there is shown a schematic drawing of an MPSiAS, having some of its pores containing trapped bacteria 40. In the line (B) of FIG. 4, the partly filled and partly empty pores are replaced by an effective continuous layer of thickness, l, and refractive index, n, where l is less than the average length h of the bacteria, since only some of the pores are filled. The line (C) of FIG. 4 shows the schematics of the mathematical model used to simulate the sensing experiments. Thus, for a given EOT shift, the model predicts the corresponding fill fraction. The refractive indices of the bacteria (n) and of the host saline solution ($n_0$) are taken to be 1.4 and 1.33 respectively, so that the only free parameter in the model is the effective thickness of the filled pores, or equivalently the "effective fill factor" (eff). This may be defined as $$\text{eff} = (l/L)^2 \qquad (3)$$

where, L is the pore depth, and the squared relation comes because the array is a 2-dimensional array. This quantity can be estimated from the model presented in line (B) of FIG. 4 to be:

$$eff = \frac{\Delta EOT/EOT}{\Delta n/n_0} \qquad (4)$$

where $\Delta(EOT)/EOT$ is the relative change of the EOT as measured during the sensing experiment, and $\Delta n = n - n_0$, is the absolute change of the refractive index due to bacteria capture. The fill fraction of the MPSiAS can directly be related to the effective fill factor as follows:

$$\text{fill fraction} = eff \cdot \left( \frac{\text{volume}_{pores}}{\text{volume}_{E.coli}} \right) \qquad (5)$$

Figure 5:
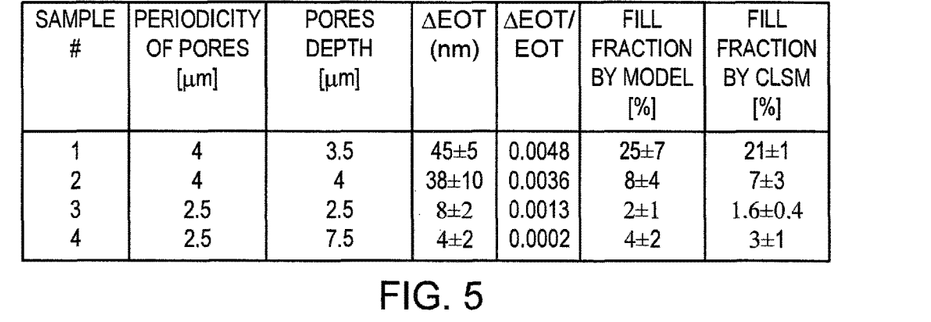
FIG. 5 shows some measured ΔEOT values for different sensing experiments and the corresponding fill fractions calculated by the model of FIGS. 4A to 4C.

Reference is now made to FIG. 5, which is a table showing some measured $\Delta$EOT values for different sensing experiments and the corresponding fill fractions calculated by the model of FIG. 4. FIG. 5 shows the fill fraction values for MPSiAS sensors, characterized by different periodicities of 2.5 and 4 µm. The values are calculated by averaging at least 5 images taken at different locations for each sensor. As is observed from FIG. 5, structures with high periodicity i.e., larger pores, exhibit greater EOT shifts, corresponding to superior bacteria capture. The model results are in fairly good agreement with the fill fraction estimated by the CLSM technique indicating that, despite of the model's approximations, it provides a reasonable description to the sensing events. For example, for sample 1, the model predicts a fill fraction of ~25%, while the CLSM data yields a fill fraction value of approximately 21%. The deviations between the fill fraction values are mainly attributed to the model assumptions. First, the model refers to the bacteria as a homogenous liquid filling the pores. This assumption oversimplifies the complex structure of the cell and its heterogeneity. Second, as the reflected light is collected normal to the pore's surface, only the intensity of the zero-order diffraction is measured. Therefore, due to typical pore morphology of the MPSiAS (see FIG. 1A) the model takes into consideration a diameter of about 25% of the opening of the pore for the effective coherent reflective surface, which is used to calculate the effective pore volume and hence the resulting fill fraction. Another cause for deviation may result from the difference in spot size from the optical data collected in the experimental sensing setup and in the CLSM. In the sensing setup, the EOT signal was measured from a single spot (with a typical diameter of 1 mm), while CLSM measurements were averaged over five different areas of the sensor's surface.

It is known from US Patent Application Publication US 2007/0108465 to C. Pacholski et al for "Porous Microstructure Multi-Layer Spectroscopy and Biosensing" that a conventional porous silicon thin film structure can be constructed having pores with two different cross sections, an outer or upper section having a larger average diameter (for a cylindrical pore distribution) and an inner or lower section, having a narrower average diameter. In that application, the pore sizes of the upper section are limited to 20 to 50 nm, as expected from prior art random porous silicon devices, while that of the lower sections are of the order of <20 nm. Therefore, the pores are incapable of measuring larger micro-organisms, as described in the current disclosure. In the Pacholsky application the structure is composed of two layers of PSi, each layer having a distribution of pores having different and random diameters, with the lower layer having smaller average diameters than the upper layer.

Figure 6A:
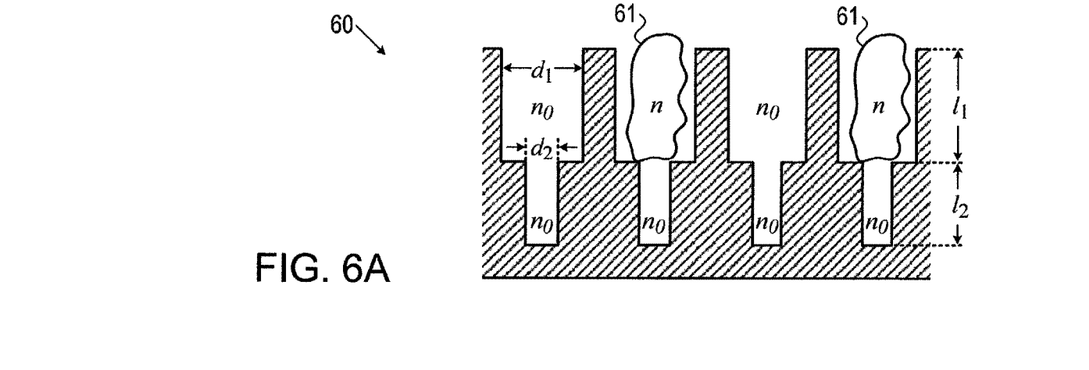
FIG. 6A illustrates schematically an alternative MPSiAS geometry, having pores with two different cross sections.

Reference is now made to FIG. 6A, which illustrates an alternative MPSiAS structure to those described hereinabove in FIGS. 1A to 5, in that it has a two-section pore structure. In contrast to what is shown in Pacholski, the implementation of FIG. 6A shows a single lamellar grating structure 60 having a single periodicity, but in which each period of the grating consists of two-sections. The upper section is wider and has a diameter $d_1$ and a length $l_1$, while the lower section is narrower having a diameter $d_2$ and a length $l_2$. If the diameter of the target cell is denoted by D, then, the pore diameters of both sections should follow the following condition:

$$d_2 < D < d_1$$

In this case, the target cells 61 are capable of penetrating into the upper section of the pores and of being captured there, but are not capable of penetrating into the lower section of the pores. The host solution, however, can flow into both sections of the pores as schematically illustrated in FIG. 6A.

Figure 6B:
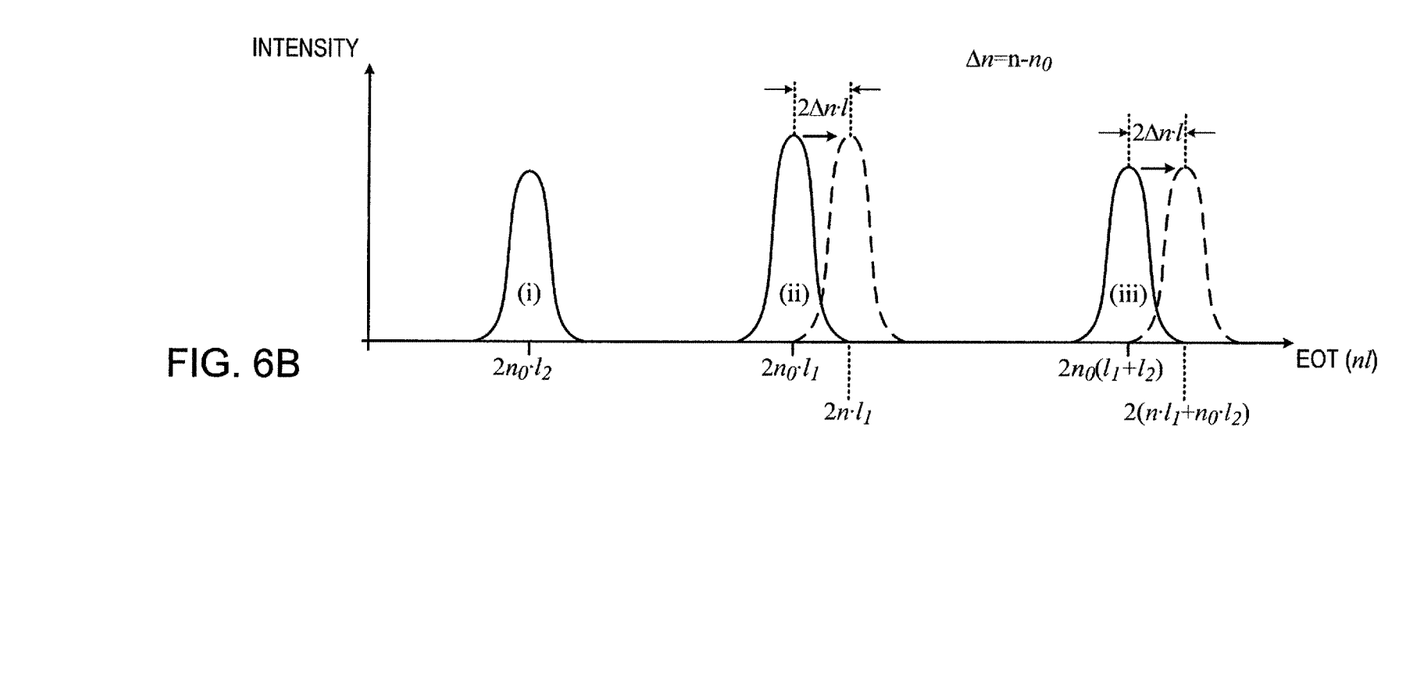
FIG. 6B shows the ensuing FTT output plot of the light reflected from such an array.

When illuminated by a white light broadband source, reflection from the grating into a set of diffraction orders occurs, again, according to the relationship between the periodicity, p, and the optical wavelength. As before, only the zero-order reflection is collected by the optics but a more complex interference pattern is obtained from the two-section pores. Reference is now made to FIG. 6B, which is a plot obtained of the intensity of the reflected light in FTT space as a function of the optical path differences EOT. Three peaks are shown marked as:
(i) $2 \cdot n_0 \cdot l_1$ (EOT of section 1 of each pore),
(ii) $2 \cdot n_0 \cdot l_2$ (EOT of section 2 of each pore) and
(iii) $2 \cdot n_0 \cdot (l_1 + l_2)$ (EOT of the total length including both sections of the pore),
where $n_0$ is the refractive index of the host analyte solution.

However, these peaks behave differently from those described in Pacholski, since the physical mechanism is different, being directly based on the optical thicknesses and the refractive indices of the host solution (with a refractive index, $n_0$) and the target cells (with a refractive index, n). On the other hand, in the Pacholski structure the effective optical thicknesses (EOTs) and the effective refractive indices of the layers are based on complex averaging over the refractive indices of the solution/target molecules with those of the porous media. Hence, the two-section MPSiAS of the present application allows direct sensing of the optical thicknesses of the host solution (in the lower section, subscripted 2, of the pores shown in FIG. 6A and the target cells (in the upper section, subscripted 1, of the pores shown in FIG. 6A, while in the Pacholski structure the EOTs measure more complex functions, that involve complicated averaging over the properties of the host/targets and the porous media in which they are embedded.

In the two-section MPSiAS of the present application, if both of the sections of the pores are filled with the host analyte solution, then any change in environmental conditions causes all three peaks to move proportionally, maintaining, at least to first order, the same ratios between them.

However, if now bacterial cells, having a refractive index n, enter the top section 1 of a pore, peaks (ii) and (iii), being dependent on $l_1$, will, assuming that $n > n_0$, shift to the right to a larger EOT value. Thus peak (ii) moves to position $2nl_1$, and peak (iii) moves to a position $2(n \cdot l_1 + n_0 \cdot l_2)$. Denoting the value of $(n - n_0)$ as $\Delta n$, each of peaks (ii) and (iii) move by a distance $2\Delta n l_1$.

Peak (i) on the other hand, being dependent only on $l_2$, does not shift, since, in the absence of a target element entry, no change has occurred to its optical path length $l_2$. Hence, the distance between the first peak $2 \cdot n_0 \cdot l_2$, which is not affected by the capture of the target cells, and the other two peaks is a measure to the number of bacteria (or target) cells which have been captured by the pores of the device, independent of environmental changes which affect the peaks in a similar manner. The greater the number of target elements captured, the larger the shift right of peaks (ii) and (iii). Furthermore, the distance between the second and third peaks can be used as a reference to eliminate random fluctuations in the signals that may cause "false alarm" events. Of course, if $n<n_0$, then the peak shifts will be towards shorter EOT levels.

This array configuration makes it possible to eliminate the effect of environmental change on the measurement of the bacterial concentration, by measuring the relative shift between the first peak (i) and the other two peaks, (ii) and (iii), whereby the shift between the peak due to the lower section and that due to the upper or both sections is used as an environmental marker.

An additional and novel advantage of such a dual cross-section pore can be implemented if the lower, narrow section of the pore is provided with target selectivity to a material which the microorganisms trapped in the upper, wide section of the pore, may secrete. Such an implementation then provides a further level of validation as to the presence and even the quantity of microorganisms trapped in the device. Thus, for instance, the lower narrower sections of the pore may contain a trapping material for combining with proteins or toxins that bacteria trapped in the upper section may secrete. The selective trapping of these materials will result in a change in the refractive index of the narrow section of the pores, which will be reflected in a further change in the EOT characteristic of the narrow section of the pores, thereby providing a secondary measure of the presence of the specific bacteria in the upper, wider section of the pores. For example, Shiga toxin-producing *E. coli* organisms (STEC) are pathogens capable of producing sporadic and epidemic diarrhea, hemorrhagic colitis, and potentially life threatening hemolyticuremic syndrome. STEC possess a number of virulence factors, and the production of Shiga toxins (Stx1 and/or Stx2) is the most critical. Detection and identification of non-O157:H7 STEC serotypes in a timely fashion are more difficult even in a laboratory setting. Thus, by using the dual cross-section pore structure (in combination with appropriate surface modification of the narrow pores with receptors for Shiga toxins (antibodies of glycans) it would be possible to distinguish between STEC and non-STEC.

It is appreciated by persons skilled in the art that the present invention is not limited by what has been particularly shown and described hereinabove. Rather the scope of the present invention includes both combinations and subcombinations of various features described hereinabove as well as variations and modifications thereto which would occur to a person of skill in the art upon reading the above description and which are not in the prior art.

We claim:

1. A system for detecting target elements in a host analyte, said system comprising:

a substrate containing an ordered array comprising a predetermined pattern of wells formed in its surface, at least some of said wells having predetermined lateral dimensions such that said target elements can fit therein;

a broadband illumination source configured to illuminate said surface of said substrate with broadband illumination over a range of wavelengths;

an optical detector disposed such that it collects illumination diffracted from said substrate, and outputs a reflected spectrum signal; and a signal processing unit, adapted to analyze said reflected spectrum signal to provide a measure of the effective optical depth of said wells, wherein at least some of said wells have a lateral dimension at least as large as those wavelengths of said illumination source which are diffracted from said substrate and detected by said optical detector, to output said reflected spectrum signal which is analyzed by said signal processing unit, such that said system can detect said target elements.

2. A system according to claim 1 wherein said signal processing unit analyzes said reflected spectrum signal using the Fast Fourier Transform.

3. A system according to claim 1 wherein said optical detector is disposed normal to said substrate, such that it collects diffracted light of zero order from said substrate.

4. A system according to claim 1, wherein said effective optical depth of said wells provides an indication of the concentration of said target elements captured within said array of wells.

5. A system according to claim 2, wherein said effective optical depth is determined from the position of a peak obtained from the results of Fast Fourier transform analysis on said reflected spectrum.

6. A system according to claim 1, wherein said ordered array of wells comprises a lamellar photonic crystal grating.

7. A system according to claim 1, wherein said substrate is a silicon chip, and said ordered array of wells are constructed by microelectronic fabrication processes.

8. A system according to claim 1, wherein said target elements are bacterial cells having dimensions larger than the wavelengths of said illumination source detected by said optical detector element.

9. A system according to claim 1, wherein said wells comprise capture probes having a high affinity to the target elements intended to be measured by said system.

10. A system according to claim 9, wherein said target elements are micro-organisms, and said capture probes are any one of antibodies, aptamers or other peptides.

11. A system according to claim 10, wherein said micro-organisms are bacterial cells, and said capture probes are specific antibodies.

12. A system according to claim 1, wherein said system is adapted to provide real time detection of microorganisms.

13. A system according to claim 9, further comprising a cell nutrient supply, such that the growth of a microorganism can be observed after application of said nutrient supply.

14. A system according to claim 1 wherein at least some of said wells include a recognition moiety adapted to said target elements to be detected.

15. A system according to claim 14, wherein said substrate comprises at least two different regions, the wells in each of said regions including a different recognition moiety, such that each of said different regions can detect different target elements concurrently.

16. A system according to claim 1, wherein at least some of said wells have at least two sequential sections having different lateral dimensions, and wherein a second section, further from said surface than a first section, has a lateral dimension less than that of said first section.

17. A system according to claim 16, wherein the dimensions of said second section are such that said target elements cannot penetrate said second section, while said host analyte can.

18. A system according to claim 16, wherein change of said measured effective optical depth of said second section of at least some wells is utilized as a marker to compensate for changes in environmental conditions that cause said effective optical depth of both of said first and second sections to change.

19. A system according to claim 16, wherein said second section is provided with sensitivity to a material which targets trapped in said first section may secrete.

20. A system according to claim 19 wherein said sensitivity provides further information regarding the level of targets trapped in said first sections of said wells.

21. A system according to claim 1 wherein at least some of said wells have a depth at least several times as large as the wavelengths of said illumination source detected by said optical detector.

22. A system according to claim 1 wherein said wells in said predetermined pattern are arranged in an ordered array of rows and columns.

* * * * *